US00PP29226P2

(12) United States Plant Patent
Koot

(10) Patent No.: US PP29,226 P2
(45) Date of Patent: Apr. 10, 2018

(54) POINSETTIA PLANT NAMED 'DUEPOBOUQ'

(50) Latin Name: ***Euphorbia pulcherrima* Willd.**
Varietal Denomination: Duepobouq

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,521

(22) Filed: Jan. 24, 2017

(51) Int. Cl.
*A01H 5/02* (2018.01)

(52) U.S. Cl.
USPC ..... Plt./307

(58) Field of Classification Search
USPC ..... Plt./307
See application file for complete search history.

*Primary Examiner* — Annette H Para
(74) *Attorney, Agent, or Firm* — C. A. Whealy

(57) ABSTRACT

A new and distinct cultivar of Poinsettia plant named 'Duepobouq', characterized by its upright to somewhat outwardly spreading and uniformly mounding plant habit; moderately vigorous growth habit; strong lateral branches; relatively late flowering habit; inflorescences with large red-colored flower bracts; and excellent post-production longevity.

1 Drawing Sheet

Botanical designation: *Euphorbia pulcherrima* Willd.
Cultivar denomination: 'DUEPOBOUQ'.

BACKGROUND OF THE INVENTION

The present invention relates to a new and distinct cultivar of Poinsettia plant, botanically known as *Euphorbia pulcherrima* Willd., and hereinafter referred to by the name 'Duepobouq'.

The new Poinsettia plant is a product of a planned breeding program conducted by the Inventor in Rheinberg, Germany. The objective of the breeding program is to create compact Poinsettia plants with strong lateral branches and attractive flower bract coloration.

The new Poinsettia plant originated from a cross-pollination made by the Inventor in July, 2011 in Rheinberg, Germany of a proprietary selection of *Euphorbia pulcherrima* Willd. identified as code number EE-0331, not patented, as the female, or seed, parent with a proprietary selection of *Euphorbia pulcherrima* Willd. identified as code number EE-0365, not patented, as the male, or pollen, parent. The new Poinsettia plant was discovered and selected by the Inventor as a flowering plant from within the progeny of the stated cross-pollination in a controlled greenhouse environment in Rheinberg, Germany in December, 2015.

Asexual reproduction of the new Poinsettia plant by terminal vegetative cuttings in a controlled greenhouse environment in Rheinberg, Germany since January, 2016 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Duepobouq'. These characteristics in combination distinguish 'Duepobouq' as a new and distinct Poinsettia plant:

1. Upright to somewhat outwardly spreading and uniformly mounding plant habit.
2. Moderately vigorous growth habit.
3. Strong lateral branches.
4. Relatively late flowering habit.
5. Inflorescences with large red-colored flower bracts.
6. Excellent post-production longevity.

Plants of the new Poinsettia differ primarily from plants of the female parent selection in the following characteristics:

1. Plants of the new Poinsettia are more compact than and not as vigorous as plants of the female parent selection.
2. Plants of the new Poinsettia flower later than plants of the female parent selection.

Plants of the new Poinsettia differ primarily from plants of the male parent selection in the following characteristics:

1. Plants of the new Poinsettia are more compact than and not as vigorous as plants of the male parent selection.
2. Plants of the new Poinsettia have thicker lateral branches than plants of the male parent selection.

Plants of the new Poinsettia can be compared to plants of *Euphorbia pulcherrima* Willd. 'Fiscor', disclosed in U.S. Plant Pat. No. 9,364. In side-by-side comparisons, plants of the new Poinsettia differ primarily from plants of 'Fiscor' in the following characteristics:

1. Plants of the new Poinsettia are more compact than and not as vigorous as plants of 'Fiscor'.
2. Plants of the new Poinsettia are more upright than and not as spreading as plants of 'Fiscor'.
3. Leaves of plants of the new Poinsettia are narrower than leaves of plants of 'Fiscor'.

4. Flower bracts of plants of the new Poinsettia are narrower than flower bracts of plants of 'Fiscor'.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant.

The photograph comprises a side perspective view of a typical flowering plant of 'Duepobouq' grown in a container.

DETAILED BOTANICAL DESCRIPTION

The aforementioned photograph and following observations and measurements describe plants grown in Rheinberg, Germany during the summer and autumn in a glass-covered greenhouse and under cultural practices typical of commercial Poinsettia production. During the production of the plants, day and night temperatures averaged 18° C. and light levels averaged 4,500 lux. Single plants were grown in 12-cm containers and were pinched one time about three weeks after planting the cuttings. Plants were 16 weeks old when the photograph and the detailed description were taken. In the following description, color references are made to Pantone Color Chart, 2015 Edition, except where general terms of ordinary dictionary significance are used.

Botanical classification: *Euphorbia pulcherrima* Willd. 'Duepobouq'.

Parentage:

*Female, or seed, parent*.—Proprietary selection of *Euphorbia pulcherrima* Willd. identified as code number EE-0331, not patented.

*Male or pollen parent*.—Proprietary selection of *Euphorbia pulcherrima* Willd. identified as code number EE-0365, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.,

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant habit and form*.—Upright to somewhat outwardly spreading and uniformly mounding plant habit; narrow inverted triangle, mounding; inflorescences with large flower bracts positioned above the foliar plane; moderately vigorous growth habit.

*Plant height*.—About 26 cm.

*Plant diameter or spread*.—About 44 cm.

*Lateral branch description*.—Quantity: Freely branching habit with about six to seven lateral branches developing after pinching. Length: About 18 cm, Diameter: About 6 mm. Internode length: About 1.3 cm. Strength: Moderately strong. Texture: Smooth, glabrous. Color: Close to 19-0230.

*Leaf description*.—Arrangement: Alternate, simple. Length: About 11.5 cm. Width: About 7.1 cm. Shape: Ovate. Apex: Apiculate. Base: Obtuse. Margin: Dentate. Venation pattern: Pinnate. Texture, upper surface: Smooth, glabrous. Texture, lower surface: Rugose, glabrous. Color: Developing leaves, upper surface: Close to 19-0230. Developing leaves, lower surface: Close to 18-0119. Fully expanded leaves, upper surface: Close to 19-0315; venation, close to 18-0328. Fully expanded leaves, lower surface: Close to 19-0230; venation, close to 17-0330. Petioles: Length: About 5.4 cm. Diameter: About 3 mm. Texture, upper and lower surfaces; Smooth, glabrous. Color, upper and lower surfaces: Close to 19-1627.

Inflorescence description:

*Inflorescence type and habit*.—Inflorescences are compound corymbs of cyathia with flower bracts subtending the cyathia; one inflorescence per lateral branch with inflorescences positioned above and beyond the foliar plane.

*Fragrance*.—None detected.

*Natural flowering season*.—Plants flower naturally during the autumn and winter under long nyctoperiod conditions; inflorescence initiation and development can be induced under artificial long nyctoperiod conditions; relatively late flowering habit, response time is about eight to nine weeks,

*Post-production longevity*.—Excellent post-production longevity; plants of the new Poinsettia maintain good substance and bract color for about twelve weeks under interior conditions.

*Inflorescence size*.—Diameter: About 20 cm. Height (depth): About 4 cm.

*Flower bracts*.—Quantity per inflorescence: About twelve. Length: About 11.5 cm. Width: About 6.5 cm. Shape: Ovate. Apex: Apiculate. Base: Obtuse. Margin: Dentate. Aspect: Mostly flat. Texture, upper surface: Glabrous; smooth, Texture, lower surface: Glabrous; rugose. Venation pattern: Pinnate. Color: Developing bracts, upper surface: Close to 19-1758. Developing bracts, lower surface: Close to 19-1662. Transitional bracts, upper surface: Close to 19-1757. Transitional bracts, lower surface: Close to 19-1664. Fully developed bracts, upper surface: Close to 19-1727; venation, close to 19-1727; color becoming closer to 19-1757 with development. Fully developed bracts, lower surface: Close to 19-1664; venation, close to 19-1664; color does not change with development. Bract petioles: Length: About 1.5 cm. Diameter: About 2 mm. Texture, upper and lower surfaces: Smooth, glabrous. Color, upper and lower surfaces: Close to 19-1725.

*Cyathia*.—Quantity per corymb: About eight. Length: About 8 mm. Width: About 5 mm. Shape: Ovoid. Texture, inner and outer surfaces: Smooth, glabrous. Color: When developing, inner surface: Close to 15-0341. When developing, outer surface: Close to 17-0336. Fully developed, inner and outer surfaces: Close to 17-0336. Nectaries: Quantity per cyathium: Typically one. Length: About 4 mm. Diameter: About 1 mm. Shape: Ovoid. Texture, inner and outer surfaces: Smooth, glabrous. Color: When developing and fully developed, inner surface: Close to 15-1062. When developing and fully developed, outer surface: Close to 13-0859.

*Peduncles*.—Length: About 3 mm. Diameter: About 1 mm. Strength: Strong. Texture: Smooth, glabrous. Color: Close to 15-0341.

*Reproductive organs*.—Stamens: Quantity per cyathium: About ten. Filament length: About 7 mm. Filament color: Close to 19-1656. Anther shape: Oval. Anther length: About 0.5 mm. Anther color: Close to 19-1627. Amount of pollen: Abundant. Pollen color: Close to 13-0858. Pistils: Quantity per cyathium: One. Pistil length: About 1 cm. Style length: About 2 mm. Style color: Close to 15-0341. Stigma shape: Crested. Stigma color: Close to 19-2024. Ovary color: Close to 17-0336. Seeds and fruits: Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 12° C. to about 40° C.

It is claimed:

1. A new and distinct Poinsettia plant named 'Duepobouq' as illustrated and described.

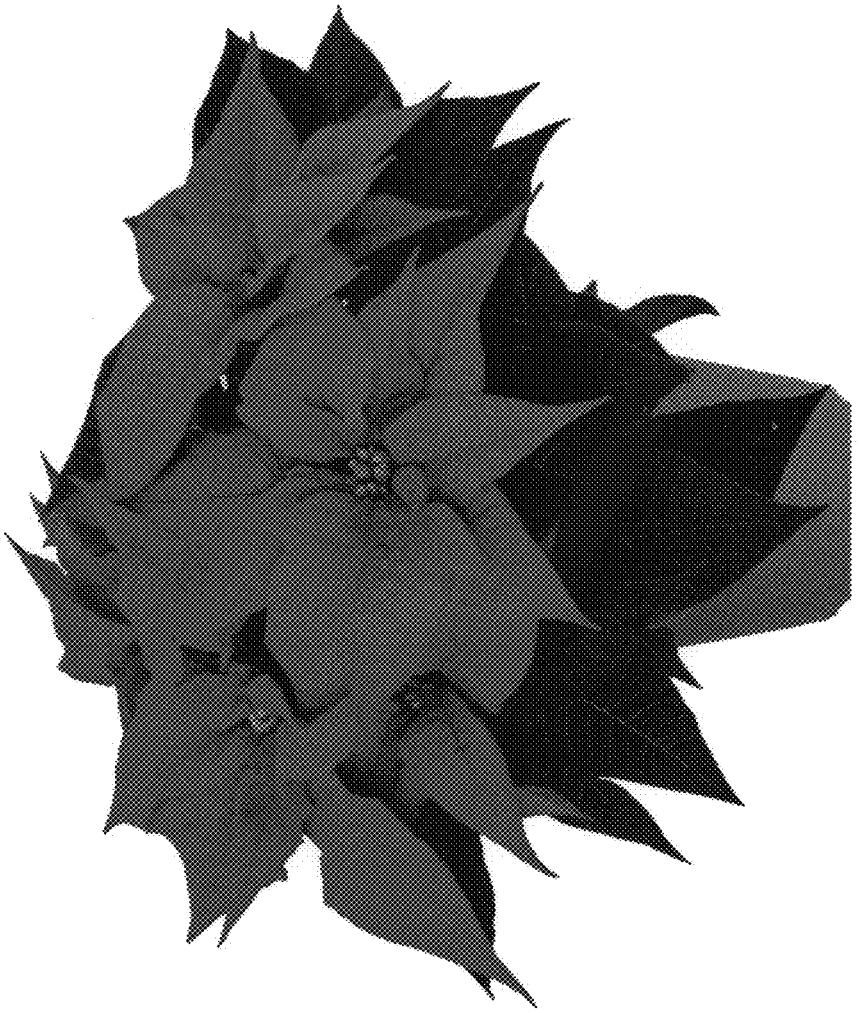

* * * * *